(12) United States Patent
Magonov et al.

(10) Patent No.: US 9,883,842 B2
(45) Date of Patent: *Feb. 6, 2018

(54) PORTABLE X-RAY MATTRESS SCANNER

(71) Applicant: ADANI Systems, Inc., Alexandria, VA (US)

(72) Inventors: Alexei Magonov, Minsk (BY); Vladimir N. Linev, Minsk (BY)

(73) Assignee: Adani Systems, Inc., Alexandria, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/641,519

(22) Filed: Jul. 5, 2017

(65) Prior Publication Data

US 2017/0311914 A1 Nov. 2, 2017

Related U.S. Application Data

(63) Continuation-in-part of application No. 14/880,196, filed on Oct. 29, 2015, now Pat. No. 9,709,694.

(51) Int. Cl.
*A61B 6/04* (2006.01)
*H05G 1/00* (2006.01)
(Continued)

(52) U.S. Cl.
CPC ............ *A61B 6/4405* (2013.01); *A61B 6/107* (2013.01); *A61B 6/52* (2013.01); *A61G 7/05* (2013.01);
(Continued)

(58) Field of Classification Search
CPC ........... G01N 21/3563; G01N 21/3581; G01N 21/89; G01N 2223/645; G01N 23/04; G01N 2223/419; G01N 23/046; G01N 23/203; G01N 2223/639; G01V 5/005; G01V 5/0016; G01V 5/0008; G01V 5/0033; G01V 5/0025; G01V 5/0041; G01V 5/0066; G01V 11/00; G01V 3/08; G01V 3/165; G01V 5/0058; G01V 5/0075
(Continued)

(56) References Cited

U.S. PATENT DOCUMENTS 6,018,562 A * 1/2000 Willson ............... G01N 23/087 378/57
6,304,629 B1 * 10/2001 Conway ................. G01N 23/04 198/502.1

(Continued)

*Primary Examiner* — Irakli Kiknadze
(74) *Attorney, Agent, or Firm* — Bardmesser Law Group

(57) ABSTRACT

A portable X-ray system includes an X-ray scanner coupled to a module for processing and visualization of digital signals; and foldable intake and output trays configured to pass an object in and out of the scanner module. The foldable intake and output trays are articulated approximately in their middle. A first drum extends substantially across an entire opening of the scanner tunnel and configured to press down on the object and pull the object inside a scanner tunnel. A second drum extends substantially across an entire opening of the scanner tunnel and configured to press down on the object and pull the object from the scanner tunnel. A radiation shield covers an opening of the scanner tunnel. Sensors detects a type of object to be scanned and to control the first drum according to the type of object to be pulled inside the scanner tunnel.

22 Claims, 17 Drawing Sheets

(51) Int. Cl.
 *G01N 23/04* (2006.01)
 *A61B 6/00* (2006.01)
 *A61B 6/10* (2006.01)
 *A61G 7/05* (2006.01)
 *A61G 7/10* (2006.01)

(52) U.S. Cl.
 CPC ........ *A61G 7/1046* (2013.01); *A61G 2210/50* (2013.01)

(58) Field of Classification Search
 USPC .............................. 378/57, 58, 62, 208, 209
 See application file for complete search history.

(56) References Cited

U.S. PATENT DOCUMENTS

| | | | |
|---|---|---|---|
| 7,310,406 B2 * | 12/2007 | Kuriyama | G01N 23/04 250/559.4 |
| 7,673,575 B2 * | 3/2010 | Dobrescu | B26D 1/24 112/122.3 |
| 8,213,570 B2 * | 7/2012 | Panesar | G01N 23/04 378/19 |
| 9,709,694 B2 * | 7/2017 | Magonov | G01V 5/0016 |
| 2010/0202694 A1 * | 8/2010 | Kabumoto | G01N 21/3581 382/190 |

* cited by examiner

PORTABLE X-RAY MATTRESS SCANNER

CROSS REFERENCE TO RELATED APPLICATIONS

This application is a continuation-in-part of U.S. patent application Ser. No. 14/880,196, filed on Oct. 29, 2015, incorporated herein by reference in its entirety.

BACKGROUND OF THE INVENTION

Field of the Invention

The invention relates to the field of engineering physics and, in particular, to X-ray scanning for dangerous or prohibited objects or substances located (or hidden) inside a mattress of an inmate in a penitentiary institution.

Description of the Related Art

Human body X-ray scanning for identifying some highly undesirable objects or substances has become critically important in view of terrorist threats. Security applications may include prevention of smuggling of drugs, precious stones and metals, as well as provision of the security at airports, banks, embassies, nuclear power centers, prisons and other high-risk locations. X-ray luggage examination in airports is currently the most efficient way to provide security of the flights. X-ray examination is also used in prisons for visitor's access control.

However, mattresses of the prison inmates are still routinely checked and searched for presence of weapons and illegal substances manually. The inmates are ordered to leave their cells and the guards perform a manual search of their cells, which includes a manual inspection of the mattresses being the most likely a hiding place for weapons or drugs. In some institutions, inmates are ordered out of the cells with their mattresses rolled up for inspection (or scanning) in a special area. This is inconvenient and inefficient. A special portable mattress X-ray scanner, which can be brought into the ward for scanning the mattresses, would make the job of the prison officers more convenient and efficient.

A similar issue exists when inmates are being transferred from one floor to another or routinely shifted to another block. The inmates have to move with mattress and all belongings they might have—and, again, the inspection of the mattresses needs to be carried out.

Accordingly, there is a need in the art for a safe, mobile X-ray scanner system that can be rolled into a facility, ward, floor or block of cells, for efficiently scanning the inmates' mattresses and for automatically detecting weapons or illegal substances hidden within the mattresses. Also such machine can be deployed in the mattress processing or storage compartment to insure that no prohibited items being transferred no matter intentionally or not.

The approach explained above is suitable for other institutions such as detention centers, homeless shelters, orphanages, etc., where a high risk of contraband of illegal items exists.

SUMMARY OF THE INVENTION

Accordingly, the present invention is related to a high-efficiency movable X-ray mattress scanner that substantially obviates one or more of the disadvantages of the related art.

In one aspect of the invention, a module for processing and visualization of digital signals and an X-ray scanner module are implemented on a mobile platform movable on wheels. A digital X-ray module includes a source of fan-shaped X-ray radiation beam with a detector of the X-ray radiation passing through a mattress being examined.

The movable X-ray mattress scanner is equipped with an input and an output tray having rollers for supporting the mattress as it is pulled in and out of the special flat-shaped opening by a drum motor. The drum motor is integrated into the X-ray mattress scanner at the scanner tunnel input opening so it can press and pull the matters inside the scanner automatically. The input and output trays can be folded for moving the scanner along narrow corridors, standard doors or on the stairs. The scanner platform is equipped with special stair stepping wheels that allow for "rolling" the scanner over the staircases without having to lift it.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE ATTACHED FIGURES

The accompanying drawings, which are included to provide a further understanding of the invention and are incorporated in and constitute a part of this specification, illustrate embodiments of the invention and together with the description serve to explain the principles of the invention.

In the drawings:

FIG. 2 illustrates a top view of the movable X-ray scanner;

DETAILED DESCRIPTION OF THE PREFERRED EMBODIMENTS

Figure 1:
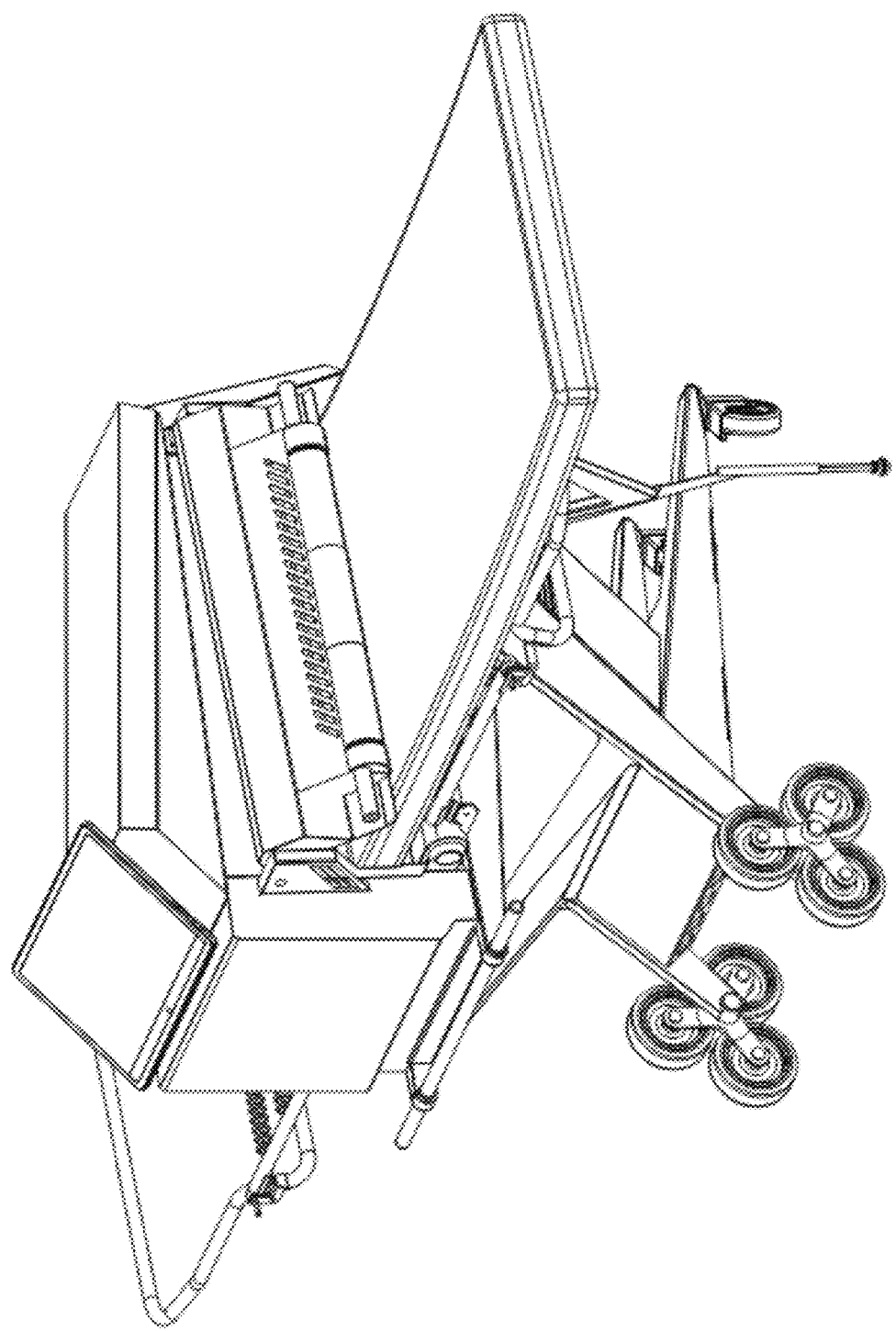
FIGS. 1 and 2 illustrate different views of the mattress scanner assembly, in accordance with the exemplary embodiment.

Reference will now be made in detail to the preferred embodiments of the present invention, examples of which are illustrated in the accompanying drawings.

In one aspect of the invention, a module for processing and visualization of digital signals and an X-ray scanner module are implemented on a mobile platform that is movable on wheels. The digital X-ray module includes a source of fan-shaped X-ray radiation beam with a detector of X-ray radiation that passes through a mattress being examined.

The mobile X-ray mattress scanner is equipped with an intake and an output tray having rollers for supporting the mattress as it is pulled in and out of the special mattress-shaped opening by a drum motor. The drum motor is integrated into the X-ray mattress scanner at the intake opening so it can press and pull the matters inside the scanner automatically. The intake and output trays can be folded for moving the scanner along narrow corridors, doors or on the stairs. The scanner platform is equipped with special stair stepping wheels that allow for "rolling" the scanner over the staircases without having to lift it.

The proposed scanner system is designed as a movable compact system with fold-out roller trays and a feeding-receiving mechanism including the drum motor. The purpose of the system is non-intrusive inspection of: the mattress, combined mattress with a pillow, inmate's belongings packed into a special flat crate. The inspection is performed by a narrow X-ray fan beam to form an image of the suspected object to visually identify threats such as metal objects, knives, shanks, razors, drugs, pills, SIM cards, money and other concealed objects within the mattress, the pillow or inside the inmate's belongings packed in the crate. The system also provides a capability of color marking of different suspicious materials on the screen, such as metal, plastic and organics by using their atomic number and density. The system also provides for automatic identification of foreign objects.

According to the exemplary embodiment, the X-ray image of the inspected object is obtained without any blind areas across the entire inspection tunnel. The acquired X-ray image is subjected to mathematical processing using substance discrimination by atomic numbers. The X-ray image is colored based on efficient atomic number calculation. The system can read a bar-code or QR code on the object being scanned and assign the X-ray image to reference data. The X-ray images are stored and archived for future reference.

According to one exemplary embodiment, a computer (i.e., an operator station) with a touch screen display is integrated into the mobile scanner system. The system can also have:

- an external mobile battery pack with a retractable cable and 110/220V voltage converter. External battery should serve as a dedicated source of main power to power-up and operate the system for at least two hours when connection to central mains grid is not possible;
- a tablet PC (comes with wireless option and fixing gear). This option allows to operate the system remotely and wirelessly using an industrial-grade protected tablet PC;
- barcode scanner, QR code scanner. The purpose of this device is to read inmate's or item assigned bar or QR codes in order to perform identification and tracking of person or item with further registration in the database and association with respective image. The bar code reader or QR code reader can be accompanied with digital camera in order to capture inmates' photos and assign them to the scanned image of the mattress or belongings;
- a UV disinfection lamp;
- a hand wash dispenser;
- stair stepping wheels;
- NAS external archiving system which is a network server-like device designed to be used as remote network storage in order to store, archive or retrieve important information. This device can be accessed and used for storing and reviewing of scan data from other systems in the facility or by a remote operator;
- a retraction mechanism for a power cord;
- an embedded USB (universal serial bus);
- an ID reader (e.g., using an RFID or proximity cards). This device can be used to identify the operator and set appropriate access level by reading a personal ID card. Also, an RFID chip can serve as presence sensor;
- a finger print reader. Reading fingerprints might be used to identify the operator and set appropriate access level, or to identify inmates and get access to individual files for further processing;
- a proximity card reader. This device can also be used to identify the operator and set appropriate access level by reading a personal ID card;
- an accreditation test object kit—a special piece of equipment designed to check and verify alignment of the system, resolution, penetration and detection capability each time the routine requires verification of the accuracy of the system; and
- a threat imitation test-object kit—a set of items imitating threats or prohibited items, such as different sorts of drugs, electronics or weapons. It is used to demonstrate detecting capability of the system in simulated "real life" conditions.

Figure 2:
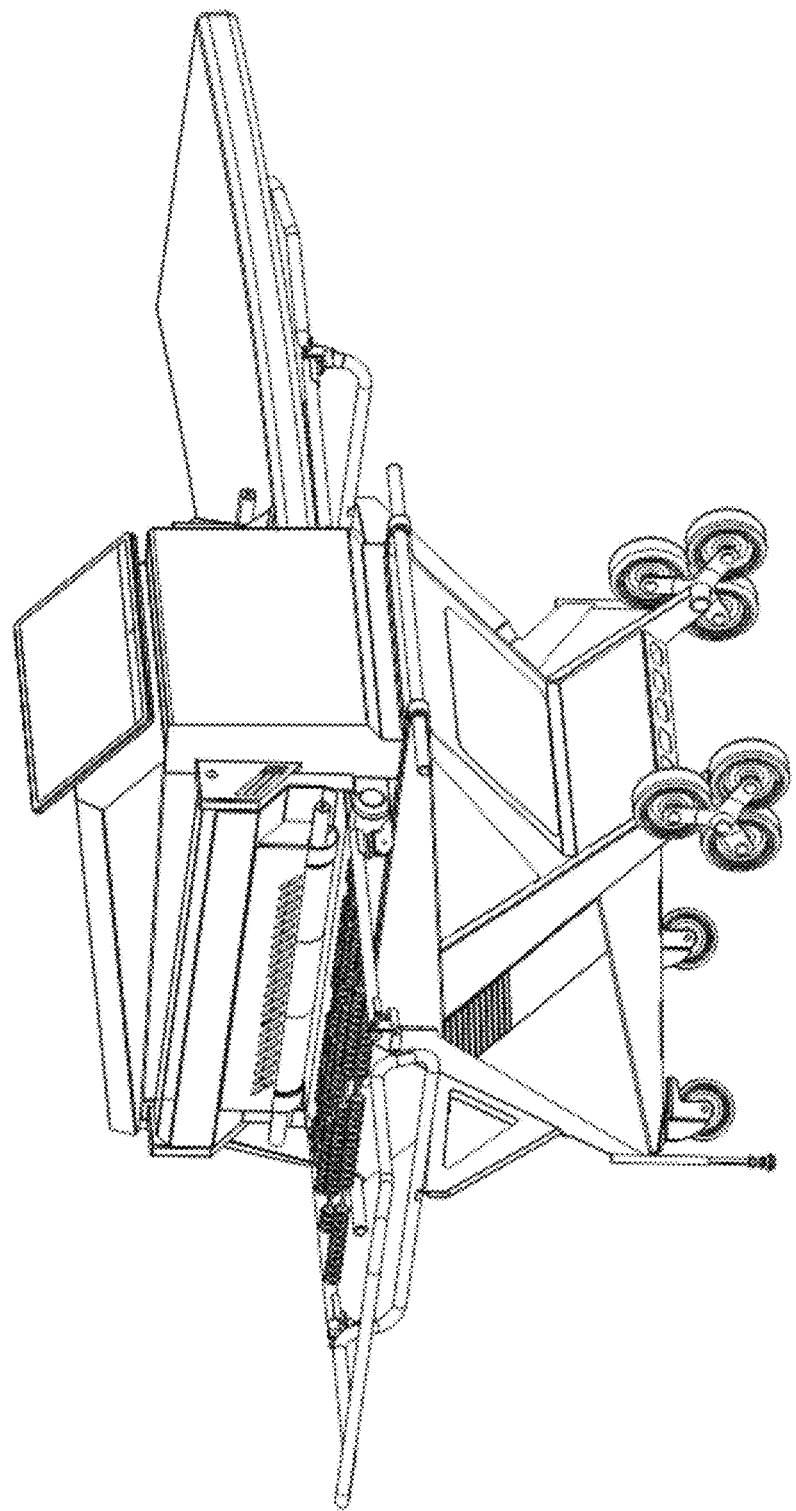
Figure 3:
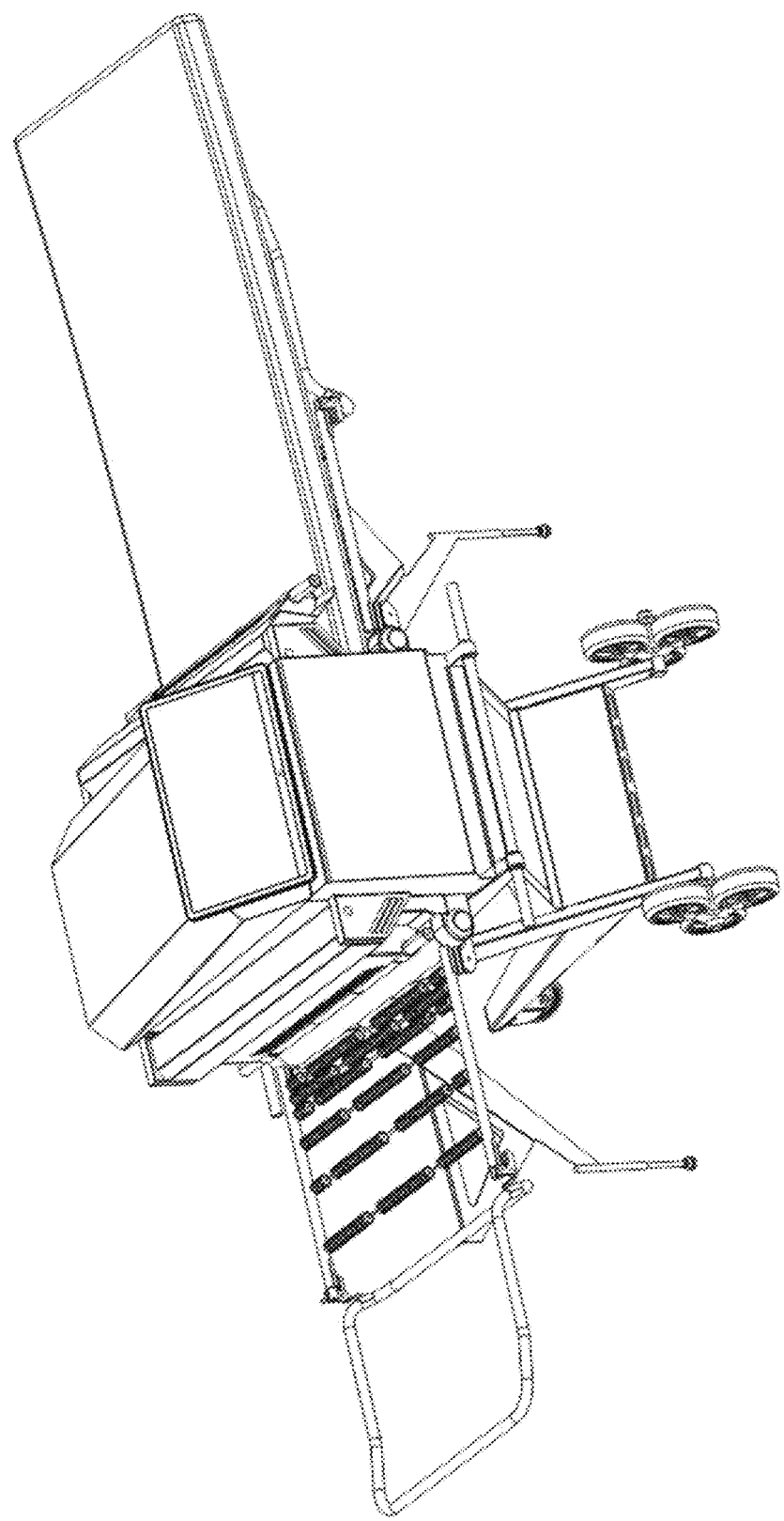
FIGS. 3 and 4 illustrate the entrance and the exit of the scanner tunnel equipped with the protective shields for protecting an officer from the fan radiation.
Figure 4:
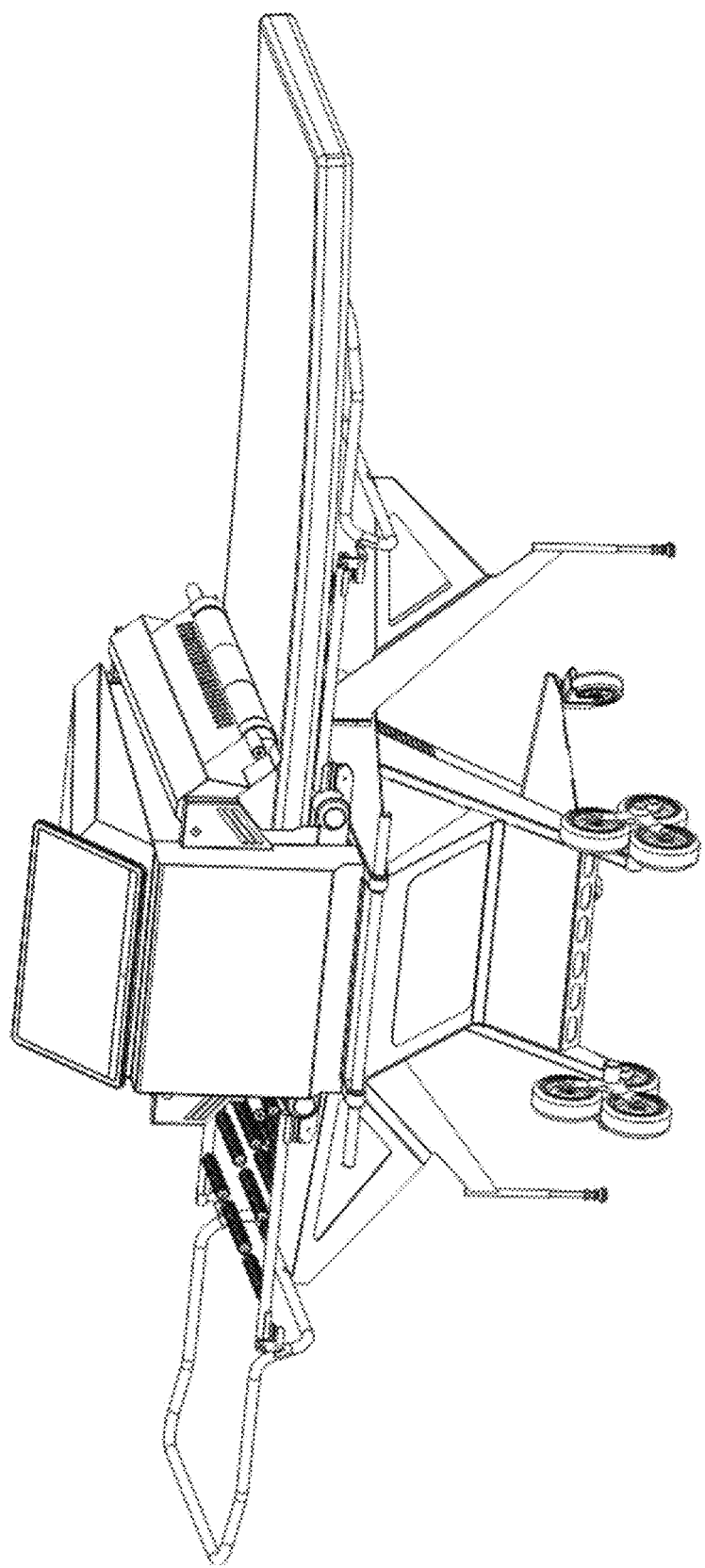

FIGS. 1 and 2 illustrate different views of the mattress scanner assembly. The mechanism for pulling mattress through the scanner includes two drum motors located on each side of the scanner tunnel. The drum motors have a system of sensors for turning on and off the motors. As can be seen from FIGS. 3 and 4 the entrance and the exit of the scanner tunnel are equipped with the protective screens for protecting an officer from the scattered radiation. In one embodiment, the protective screens are made out of lead vinyl or lead rubber.

Figure 5:
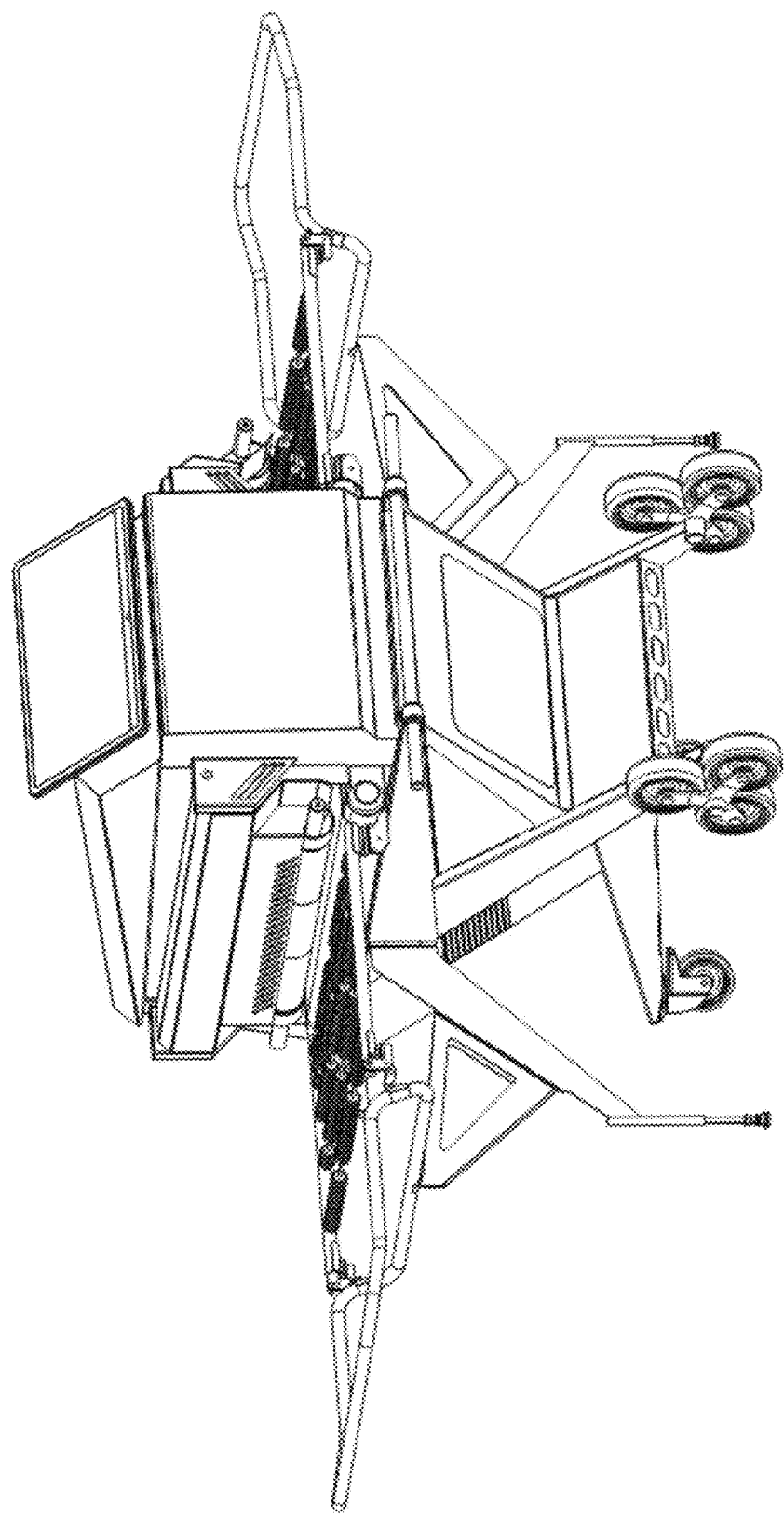
FIGS. 5 and 6 illustrate the scanner assembly with the protective screens, in accordance with the exemplary embodiment.
Figure 6:
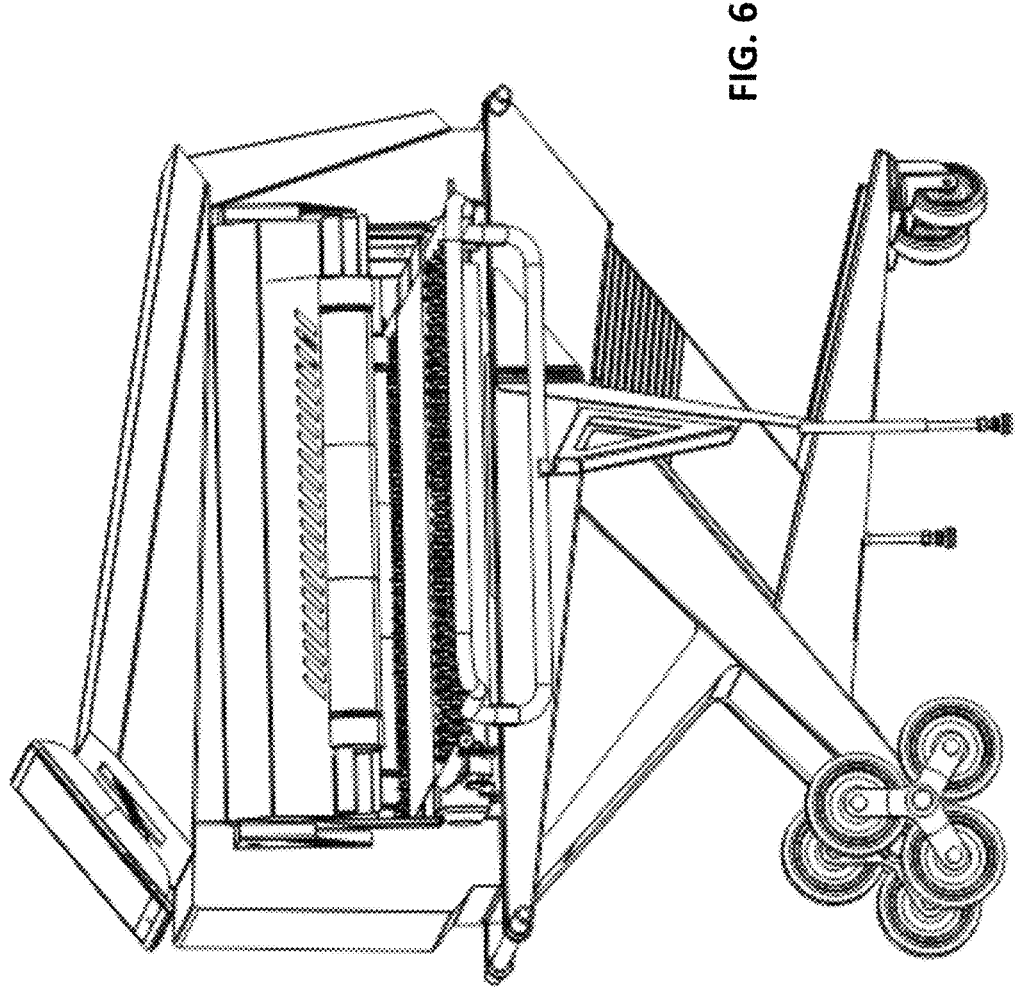
Figure 7:
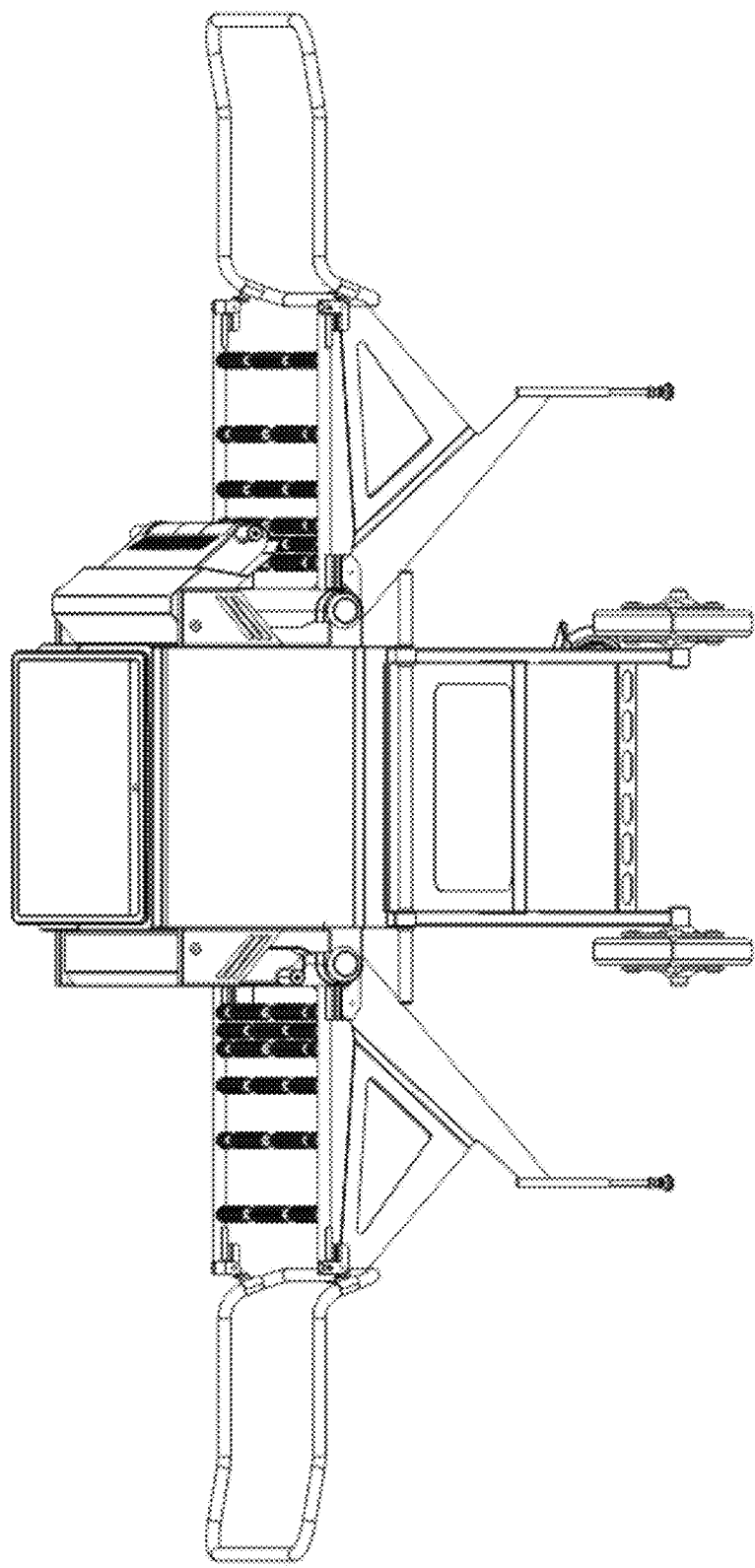
FIG. 7 illustrates the scanner with both trays unfolded on each side of the scanner.
Figure 8:
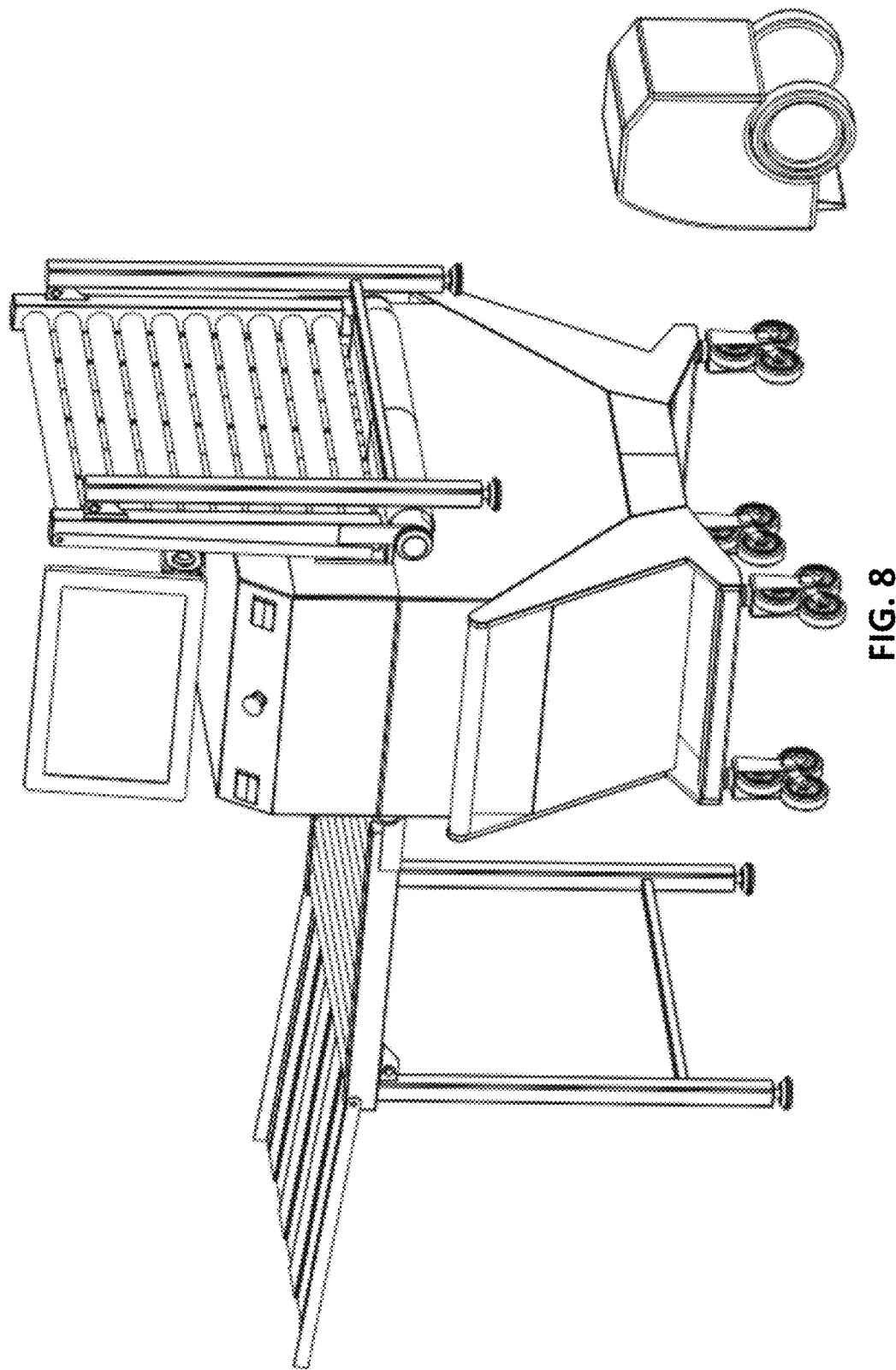
FIG. 8 illustrates that the exemplary scanner can be used with an external power source that can be rolled in with the scanner.

The protective screens can also be seen in FIGS. 5 and 6. FIG. 7 illustrates the scanner with both trays unfolded on each side of the scanner. The exemplary embodiment includes special stair stepping wheel that can be seen in FIG. 6 and FIG. 8. These wheels consist of sets of three wheels, arranged in a "star" pattern, that rotate about their own axels independently. Note that the exemplary scanner is very lightweight and can be moved around the building or between the prison cells easily. The exemplary scanner can be used with an autonomous external power source that can be rolled in with the scanner as shown in FIG. 8. The internal power source can provide for continuous operation of the scanner up to two hours.

Figure 9:
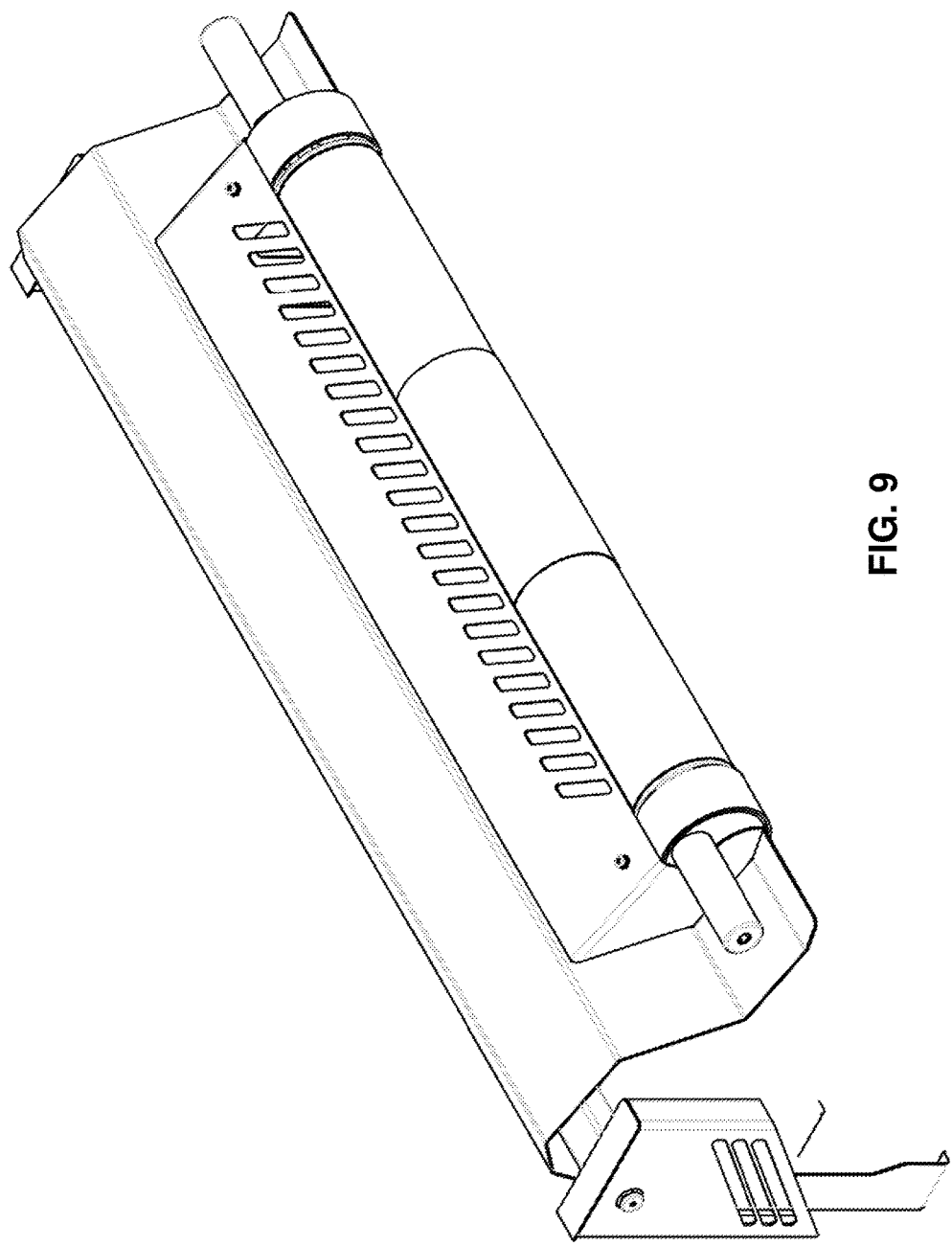
FIG. 9 illustrates a drum motor assembly with a radiation shield.
Figure 10:
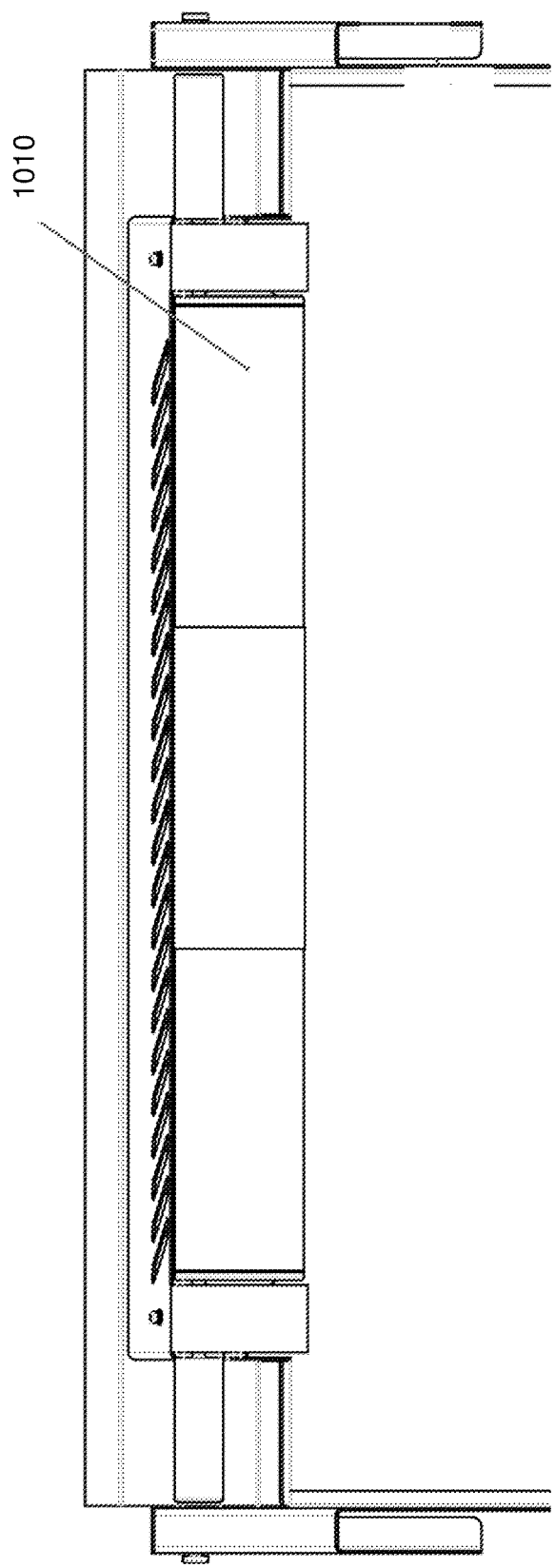
FIG. 10 illustrates a top view of the drum motor having a drum and the radiation shield.

FIG. 9 illustrates a drum motor assembly with a radiation shield. FIG. 10 illustrates a top view of the drum motor having a drum 1010 and the radiation shield.

Figure 11:
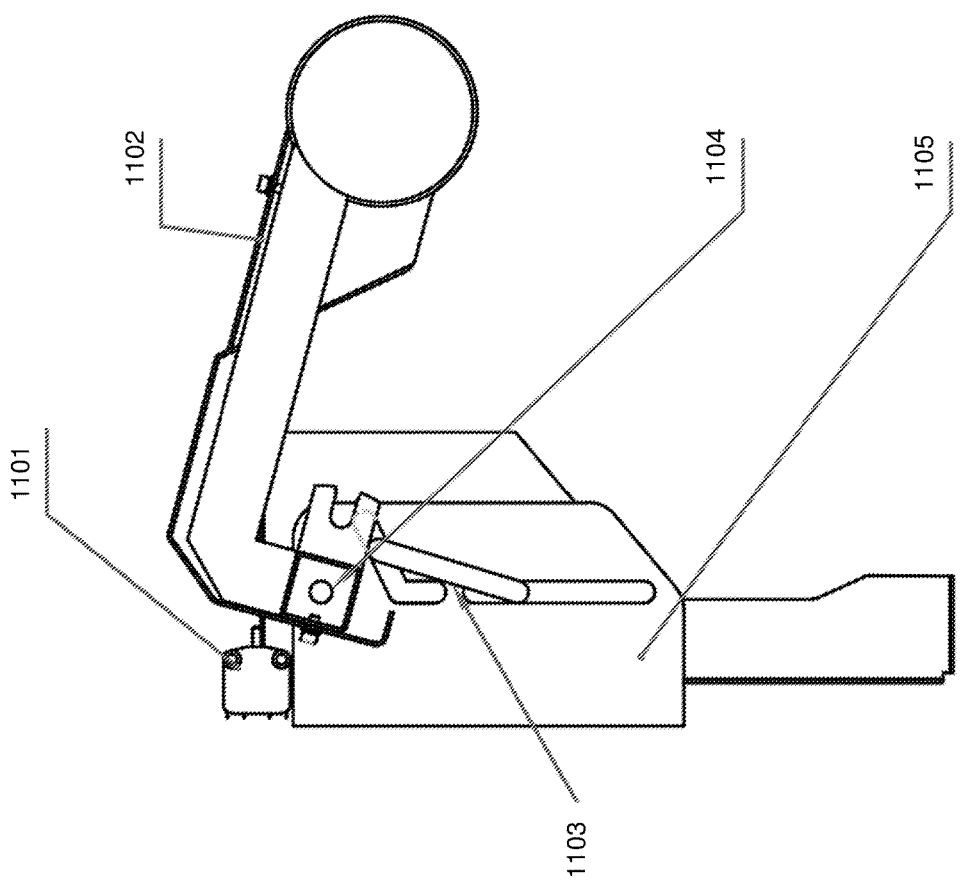
FIG. 11 illustrates a side view of the drum motor assembly with a radiation shield.

FIG. 11 illustrates a side view of the drum motor assembly with a radiation shield. The drum motor assembly includes a switch 1101. A radiation protective shield 1102 is located over the rotational drum. The drum and the protective shield can move about axis 1104 to accommodate the shape of the object being scanned. The intermediate positions of the rotor are fixed by a fixating hinge 1103. The drum assembly is attached to the body of the scanner by a bracket 1105. Each drum motor has a sensor that tells the system what is inserted (mattress or box with belongings) and the system then selects an appropriate algorithm or at certain position prevents system to be started and X-ray emission to be generated.

According to the exemplary embodiment, the scanner can be controlled by a touch screen display although a hardware keyboard can also be used. The integrated bar code scanner is also controlled by the touch screen. The scanner has sensors for automated detection of a type of object to be scanned—i.e., a mattress, pillow or a container with inmate's belongings. The scanner can be used to scan an ID tag which attached to inmate clothes or wristband or markings of belongings or mattresses.

The system obtains the information on what to be scanned (mattress or crate) by monitoring the compression unit sensor position. There are three possible scenarios (see process diagram): mattress, crate, opened portal (this mode is for service and blocks any kind of operation). Therefore, when the sensor tells the system about the type of object, the software provides a hint in form of picture and visual diagram on how to properly place the object and how to proceed. Thus, each step of system operation can be accompanied by appropriate hint. The system defines the direction of scanning by reading on which side the sensor is activated. The scanner automatically detects an area where concealed objects are located and displays them to the operator in a special way—e.g., having colored rectangular overlays or frames. The system enables coloring of suspicious areas and objects in it and introducing of rectangular marking to respective area. The operator can perform tagging of each area with special marks for further processing.

Figure 12A:
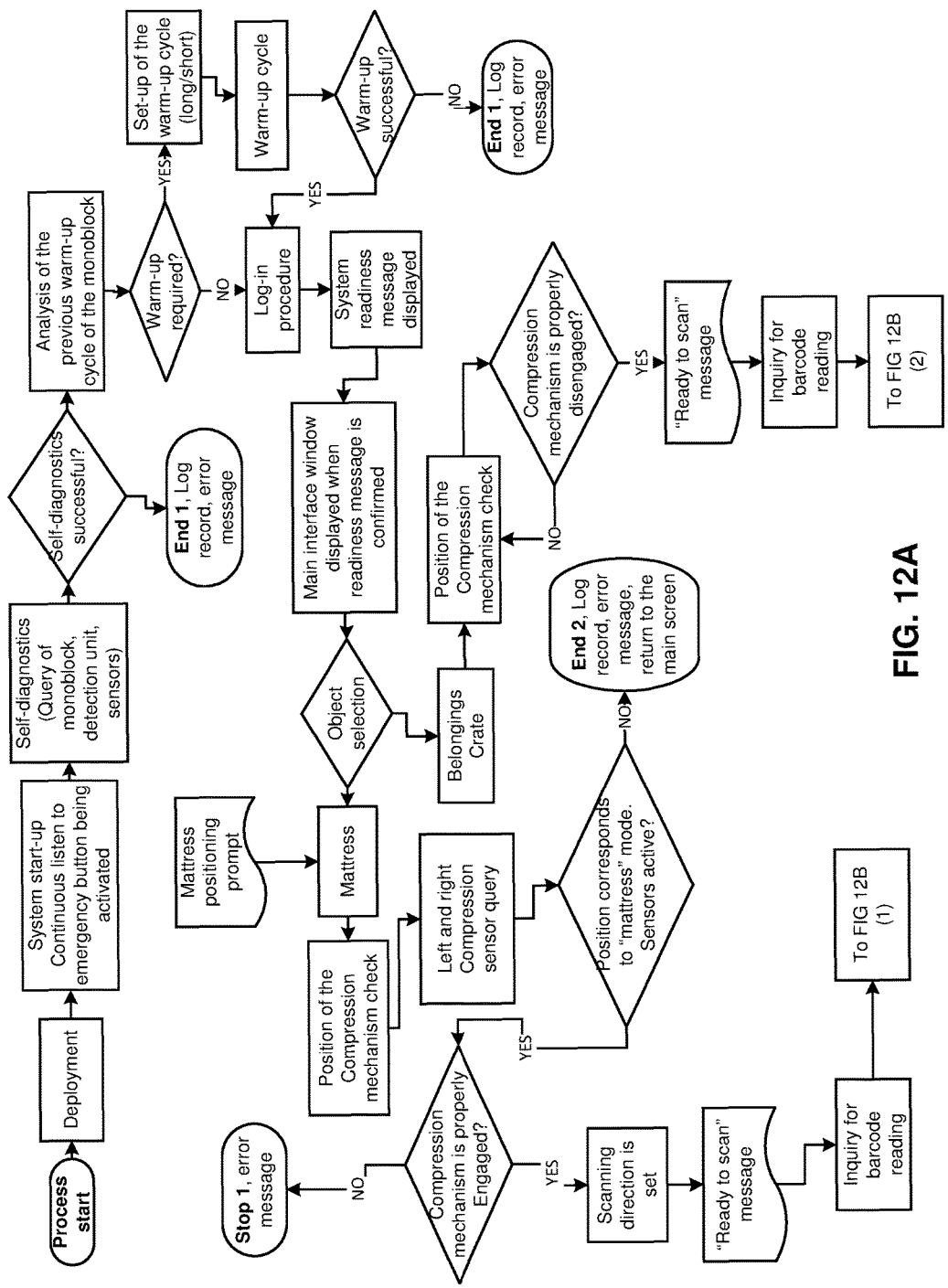
FIGS. 12A and 12B illustrate a flow chart of a scanner workflow.
Figure 12B:
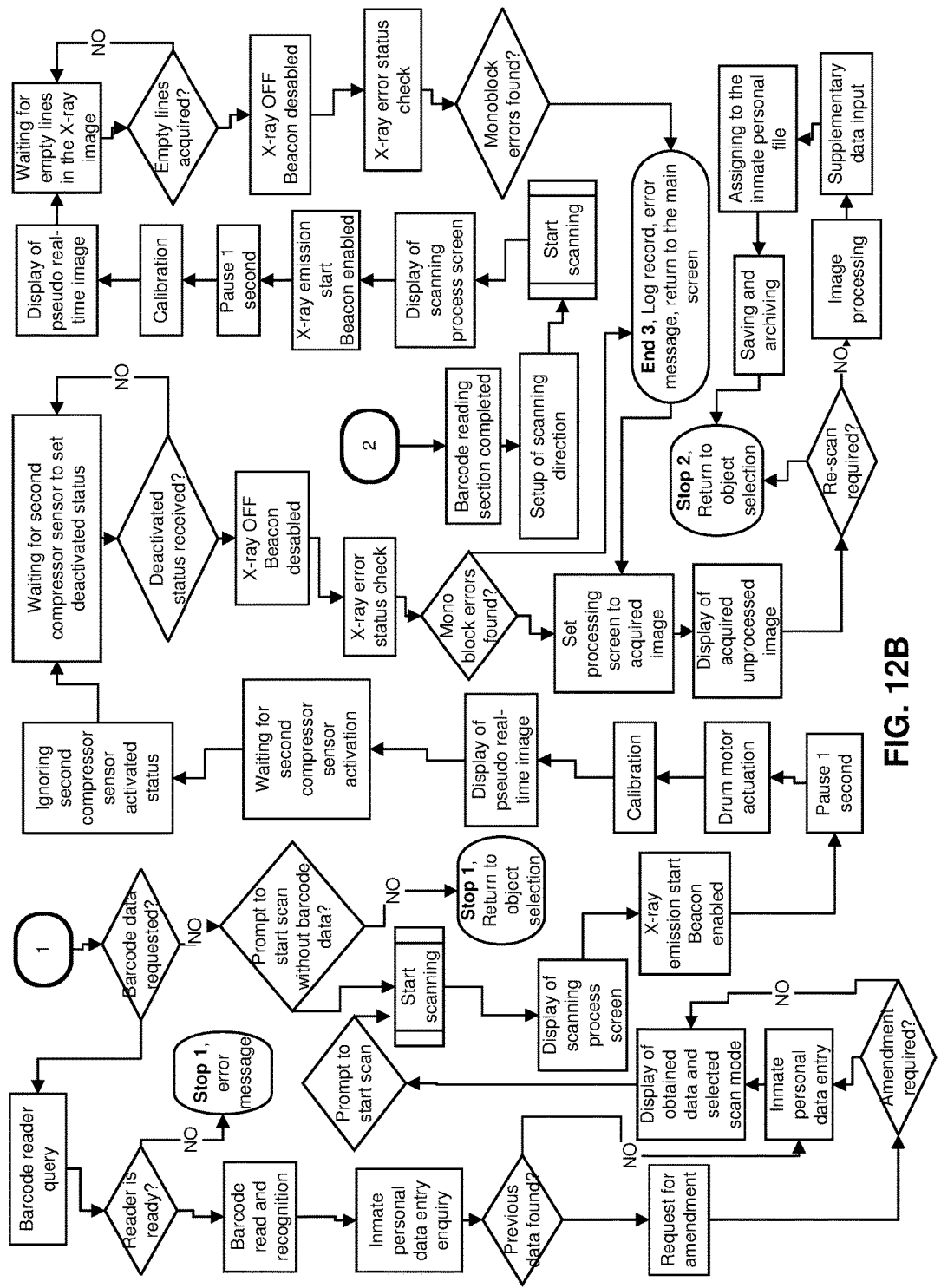

The mobile X-ray mattress scanner includes a special image processing software, which automatically detects suspected objects (image anomalies) based on the fact that mattress has a very consistent material and any images displaying anything but the material of the mattress are analyzed for presence of forbidden objects or drugs, etc. Any abnormalities detected while processing raw data obtained from digital scanning subsystem of the unit will be displayed within the visual representation of the pre-processed image. The algorithm of material discrimination provides coloring of organic, non-organic, metal and plastic objects which, and further visual analysis of the image can be used to define the objects as a threat. The image processing software uses a unique algorithm for anomalies detection on a quasi-homogeneous low-contrast background. FIGS. 12A and 12B illustrate a work flow of a scanner, in accordance with the exemplary embodiment.

In FIG. 12A, the deployment of the scanner begins. The system listens to emergency button activation. The scanner queries the sensor of the solid state detection unit. If the self-diagnostics is successful, the scanner analyses the previous warm up cycle of the X-ray source. Otherwise, the startup ends and the error message is logged. If the scanner warm up is required, the warm up cycle is set up and the worm up cycle is executed. If the warm up is successful, the process goes to login procedure. Otherwise, the process ends and the error message is logged. The system readiness message is displayed to an operator on the screen. After the readiness message is confirmed, the main interface window is displayed. The object selection and direction for scanning is made. If the object is a mattress, the scanner prompts for mattress position.

Then, the scanner checks the position of the compression mechanism by querying right and left compression sensors. If the position corresponds to a "mattress" mode and the sensors are active, the scanner checks if the compression mechanism is properly engaged. Otherwise an error message is logged. Then, the scanning direction is set and the "ready to scan" message is displayed. The scanner makes an inquiry for barcode reading and the process moves to FIG. 12B (branch 1). If the position mechanism is properly disengaged, the "ready to scan" message appears on the user screen. The inquiry for the barcode reading is made and the process moves to FIG. 12B (2).

In FIG. 12B (branch 1), if the barcode data is requested, the scanner queries the barcode reader. If the reader is ready, the barcode reading and recognition are performed. Otherwise, the error message is displayed, with a "retry", "skip" or "cancel" prompt. The inquiry for inmate personal data is made. If the previous data is found, the request for amendment of data is made and if the amendment is required, the inmate personal data is entered. The inmate's data and selected scan mode are displayed and the prompt to scan is shown. The scanning is started and the scanning process screen is displayed. The X-ray emission is started and the signal beacon is enabled. The system pauses for 1 second and the drum motor actuation starts. The calibration is performed and a pseudo real-time image is displayed. The system waits for activation of the second compression sensor and, continuing listening to the sensor status until it provides an "off" status . . . . Then, the scanner waits for the second compressor deactivation status to be set.

Once the deactivation status is received, the X-ray OFF beacon is disabled. The scanner checks for X-ray errors. An error message is displayed if errors found. Error reading data is logged. The processing screen is set to acquired image processing mode. The acquired unprocessed image is displayed, and basic automatic processing is applied. If the re-scan is required the scanner process returns to object selection step. Otherwise, the image processing is executed with supplemental data input. The resulting image is assigned to the inmate personal file and saved into the archive. Then the process returns to the object selection step.

In FIG. 12B (branch 2), the barcode reading section is completed and scanning direction is set up. Then, the scanner starts scanning the object and the scanning process is displayed on the screen. The X-ray emission starts and the beacon is enabled. The scanner pauses for 1 second for calibration. The pseudo real-time image is displayed. The process waits for empty lines in the X-ray image. If the empty lines are acquired, the X-ray OFF beacon is disabled. The scanner checks for X-ray error status. If there are any errors—the message is displayed. A query is logged. If the error is found, the process ends and the error is logged and the display returns to the main screen.

Figure 13:
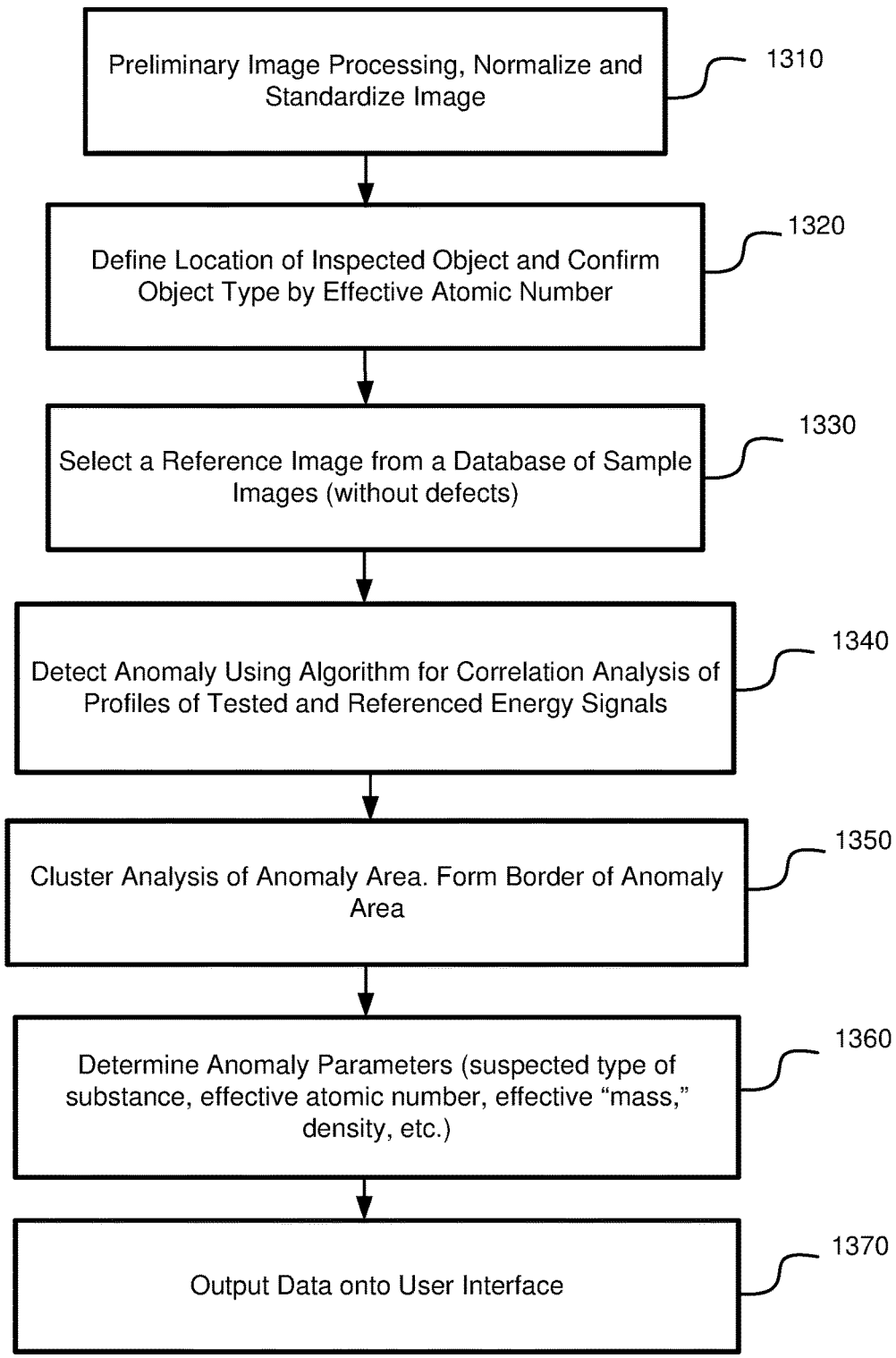
FIG. 13 illustrates a flow chart of a method for detection of anomalies in the scanned image, in accordance with the exemplary embodiment.

FIG. 13 illustrates a flow chart of a method for detection of anomalies in the scanned image, in accordance with the exemplary embodiment. In step 1310, the scanner performs preliminary image processing. The image is normalized and standardized at this point. In step 1320, the scanner defines location of inspected object and confirms the object type (e.g., mattress, pillow, a crate with belongings, etc.) using effective atomic number. In step 1340, the scanner process detects anomalies using an algorithm for correlation analysis of profiles of tested and referenced (i.e., sample) energy signals.

In step 1350, the scanner process performs cluster analysis of anomaly area and forms a border of the anomaly area. Then, in step 1360, the process determines the anomaly parameters, such as a suspected type of substance, an effective atomic number, an effective "mass," density, etc. The scanner process outputs data onto a user interface in step 1370.

Figure 14:
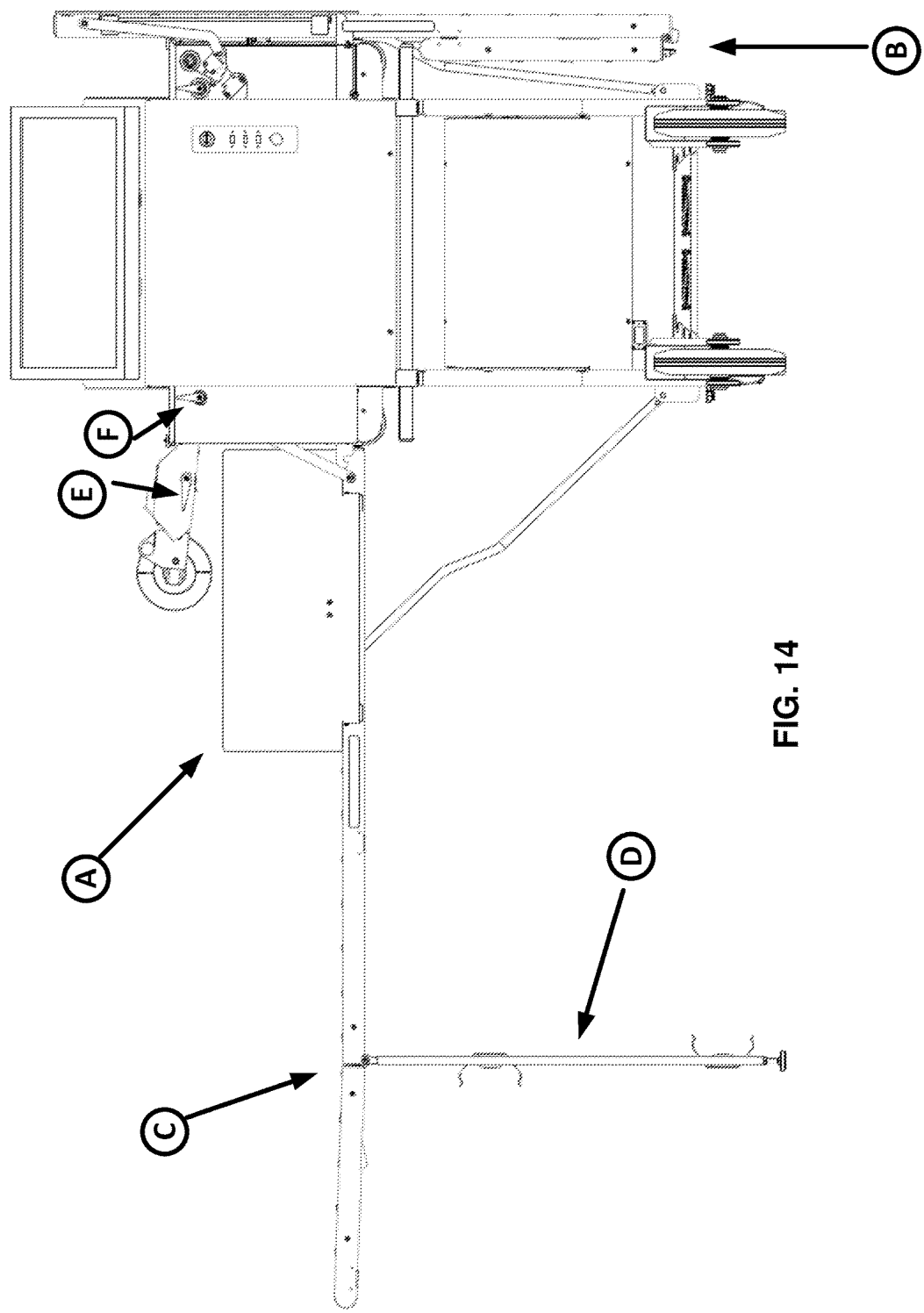
FIGS. 14, 15 and 16 illustrate additional features of another embodiment of the scanner.
Figure 15:
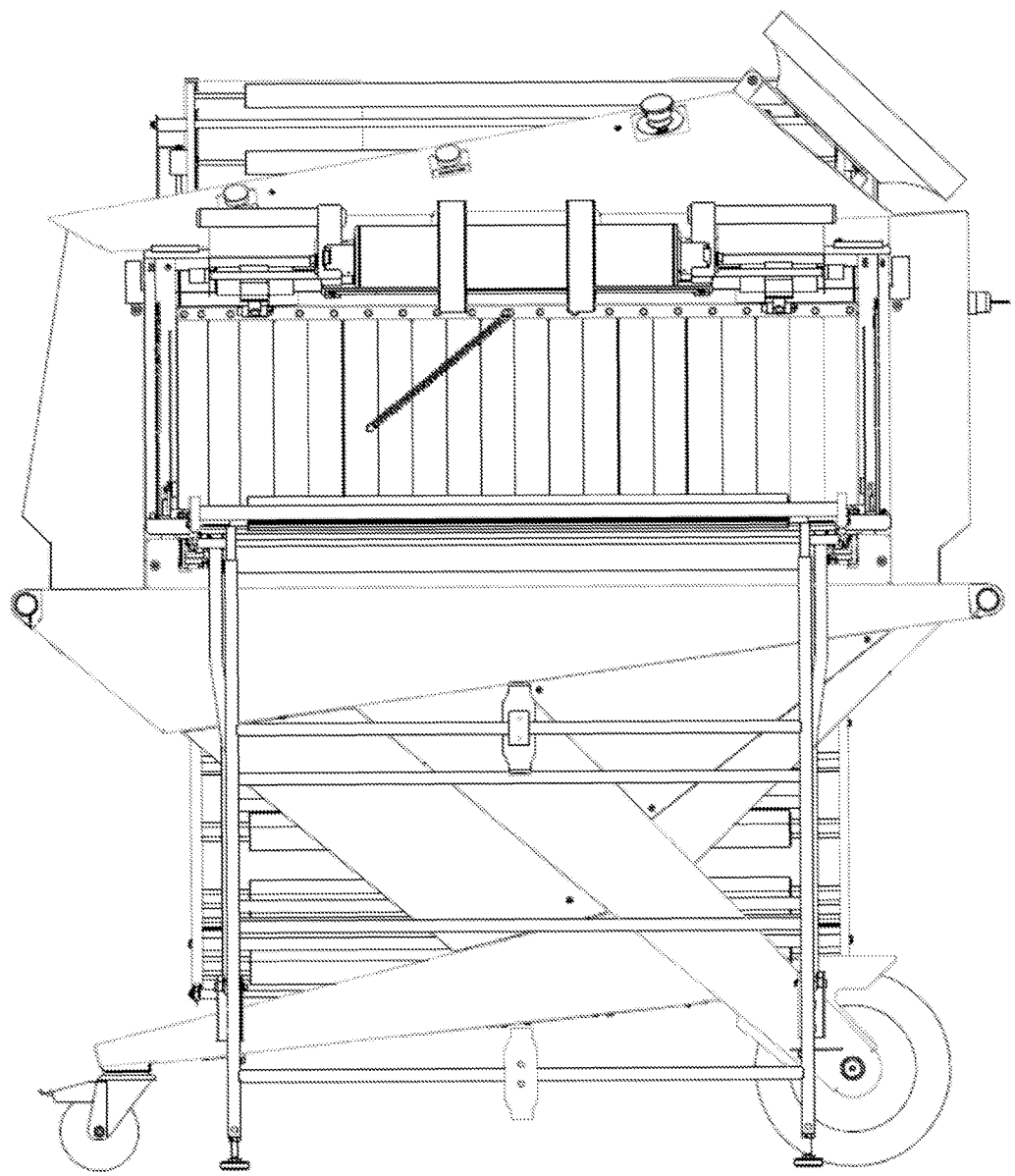
Figure 16:
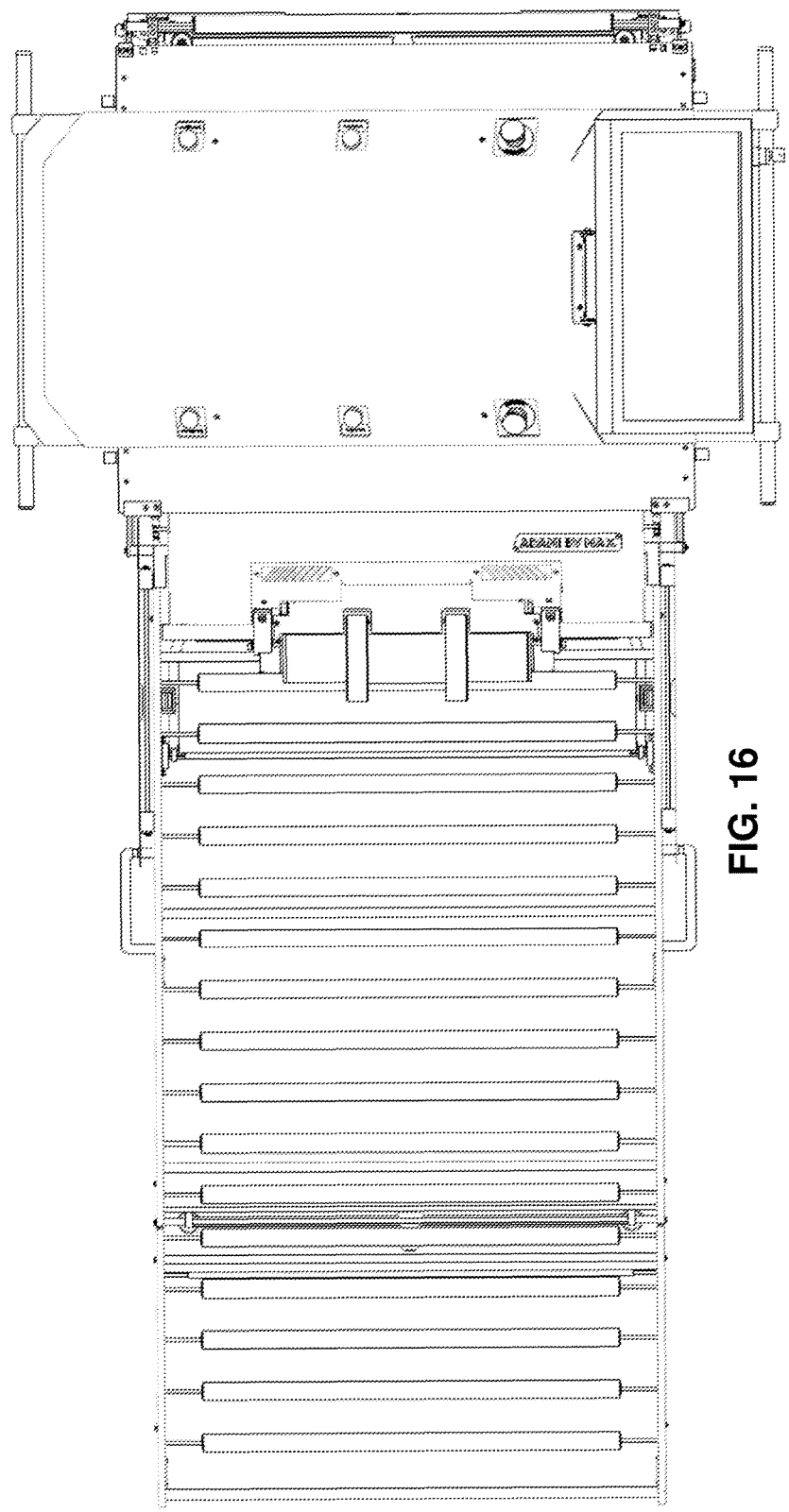

FIGS. 14, 15 and 14 illustrate additional features of another embodiment of the scanner. FIG. 14 shows a side view of the scanner, FIG. 15 shows another side view, and FIG. 16 shows a top plan view. As may be seen in these figures, the folding intake and output trays may be articulated at a point roughly ⅔ of the way out (see arrow C in FIG. 15). An additional support extending to the floor may also be provided (see arrow D in FIG. 15). Additional radiation screens (see arrow A in FIG. 15) may be located near the tunnel openings. Arrow B in FIG. 15 shows the tray in a folded position. Arrows E and F in FIG. 15 refer to locking levers that permit rotation of the drum assembly.

Having thus described a preferred embodiment, it should be apparent to those skilled in the art that certain advantages of the described method and apparatus have been achieved.

It should also be appreciated that various modifications, adaptations, and alternative embodiments thereof may be made within the scope and spirit of the present invention. The invention is further defined by the following claims.

What is claimed is:

1. A portable X-ray system comprising:
an X-ray scanner coupled to a module for processing and visualization of digital signals;
foldable intake and output trays configured to pass an object in and out of the X-ray scanner,
wherein the foldable intake and output trays are articulated either approximately in their middle or at approximately at ⅔ of their length;
a first drum that extends substantially across an entire opening of a scanner tunnel and configured to press down on the object and pull the object inside the scanner tunnel;
a second drum that extends substantially across an entire opening of the scanner tunnel and configured to press down on the object and pull the object from the scanner tunnel;
a radiation shield configured to cover an opening of the scanner tunnel; and
sensors configured to detect a type of object to be scanned and to control the first drum according to the type of object to be pulled inside the scanner tunnel.

2. The system of claim 1, wherein:
the module for processing and visualization of the digital signals acquires reference images from a database and compares them against a scanned image to detect anomalies on a quasi-homogeneous low contrast image background;
the anomalies are detected by the effective atomic number and by a calculated density; and
the detected anomalies are automatically rendered to an operator using color marks in a form of rectangular frames shown around suspect objects.

3. The system of claim 1, further comprising a compression mechanism coupled to the first drum and configured to press down on the object.

4. The system of claim 3, wherein the compression mechanism is automatically turned off, if the object to be scanned is a crate.

5. The system of claim 1, wherein the scanner is configured to scan any of:
a mattress;
a pillow; and
a flat crate.

6. The system of claim 1, wherein the radiation shield is made from lead vinyl or lead rubber.

7. The system of claim 1, wherein the X-ray scanner includes an autonomous mobile power source.

8. The system of claim 1, wherein the X-ray scanner includes a QR code reader and/or a bar code reader.

9. The system of claim 1, wherein each the X-ray scanner uses an external network archiving system for acquiring the reference images.

10. The system of claim 1, wherein the module for processing and visualization of the digital signals is configured to detect the anomalies using an algorithm for correlation analysis of profiles of tested and referenced energy signals.

11. The system of claim 1, further comprising any of:
an accreditation test object kit; and
a threat imitation test-object kit.

12. The system of claim 1, further comprising any of:
an embedded USB;
an ID reader;
a finger print reader; and
a proximity card reader.

13. The system of claim 1, wherein the module for processing and visualization also determines density of the object.

14. The system of claim 1, further comprising additional radiation screens extending from the scanner along the input and output trays.

15. The system of claim 1, wherein each of the input and output trays includes a support extending from a point of articulation to a floor.

16. A portable X-ray system comprising:
an X-ray scanner coupled to a module for processing and visualization of digital signals;
foldable intake and output trays configured to pass an object in and out of the X-ray scanner;
a first drum that extends substantially across an entire opening of a scanner tunnel and configured to press down on the object and pull the object inside the scanner tunnel;
a second drum configured to pull the object from the scanner tunnel; and
a sensor configured to detect a type of object to be scanned and to control the first drum according to the type of object.

17. The X-ray system of claim 16, wherein the foldable intake and output trays are articulated approximately in their middle.

18. The X-ray system of claim 16, wherein the foldable intake and output trays are articulated either approximately at approximately at ⅔ of their length.

19. The X-ray system of claim 16, further comprising a radiation shield configured to cover an opening of the scanner tunnel.

20. The X-ray system of claim 16, wherein the second drum extends substantially across an entire opening of the scanner tunnel.

21. The X-ray system of claim 16, further comprising stair stepping wheels attached to the X-ray scanner.

22. A portable X-ray system comprising:
an X-ray scanner coupled to a display;
foldable intake and output trays configured to pass an object in and out of the X-ray scanner;

a first drum that extends substantially across an entire opening of a scanner tunnel and configured to pull the object inside the scanner tunnel;
a second drum configured to pull the object from the scanner tunnel; and
a sensor configured to detect a type of the object, wherein operation of the first drum is controlled based on the type of object.

\* \* \* \* \*